United States Patent [19]

Beard

[11] Patent Number: 4,961,727
[45] Date of Patent: Oct. 9, 1990

[54] DISPENSING PACKAGE

[76] Inventor: Walter C. Beard, South St., Middlebury, Conn. 06762

[21] Appl. No.: 271,718

[22] Filed: Nov. 16, 1988

[51] Int. Cl.⁵ ............................................. A61M 11/00
[52] U.S. Cl. ..................................... 604/75; 604/212; 128/200.22
[58] Field of Search .................... 604/75, 94, 212, 316; 128/200.14, 200.22; 239/327, 490

[56] References Cited

U.S. PATENT DOCUMENTS

| 2,796,294 | 6/1957 | McKinnon | 239/327 |
| 2,987,261 | 6/1961 | McCuiston et al. | 239/310 |
| 4,015,753 | 4/1977 | Bennett | 239/327 |

Primary Examiner—Randall L. Green
Assistant Examiner—David H. Willse
Attorney, Agent, or Firm—Dallett Hoopes

[57] ABSTRACT

A dispensing package adapted for delivering medicine to a nasal cavity for absorption into the bloodstream comprises a flexible-walled container having a discharge head with a swirl chamber and a dip tube depending therefrom into the container. In use, the container is squeezed to drive liquid up the dip tube and into the swirl chamber to be discharged upwardly into the nasal cavity in the form of a fountain of relatively large droplets. The swirl chamber operates in the absence of air.

9 Claims, 1 Drawing Sheet

DISPENSING PACKAGE

BACKGROUND OF THE INVENTION

1. Field of the Invention

This invention relates to a dispensing package for administering a medical preparation to a human nasal cavity. More specifically, the invention relates to a package having flexible walls and an upwardly directed dispensing orifice preceded by a swirl chamber operating in the absence of air and adapted in dispensing the preparation to break it up into a fountain of relatively large droplets, as opposed, for instance, to an aerosol spray.

2. Description of Related Art including Information Disclosed under §§1.97 to 1.99

The prior art is replete with dispensing packages of the squeeze bottle type adapted to deliver liquid in spray form. An example is shown in the U.S. Pat. No. 3,519,208 which issued July 7, 1970 to P. A. Marchant wherein the squeeze bottle is provided with a plug having a dip tube extending down into the liquid. A space is provided in the plug to permit air from above the liquid to blend in with the liquid as the liquid dispenses in spray form. Other examples of such dispensers wherein air is blended along with the dispensing liquid are U.S. Pat. No. 2,642,313 issued June 14, 1949; U.S. Pat. No. 2,658,797 issued Nov. 10, 1953; U.S. Pat. No. 4,020,979 issued May 3, 1977.

The prior art also includes flexible-walled containers having inner rupturable capsules so that just prior to use the inner capsule can be ruptured by squeezing the outer container allowing the materials in the inner capsule and the outer container to contact, react or dissolve immediately prior to use. Examples are shown in U.S. Pat. No. 2,687,130 issued Aug. 24, 1954 and U.S. Pat. No. 4,540,089 issued Sept. 10, 1985.

The benefits of administration of medical preparations by way of the soft tissue in the nasal cavity have been recognized recently. More specifically, the administration of an aspirin solution, for instance, through the nose to engage on the soft tissue in the cavity has been found to be almost as fast acting as an intravenous injection; much more rapid in effect than oral administration.

The importance of speed in getting aspirin actually into the bloodstream in the treatment of migraine headaches, for instance, has been indicated by clinical studies:

If taken in the early stages of an attack, aspirin may be of benefit by impairing platelet aggregation. This aggregation precedes serotonin release from platelets, an event which may be of considerable importance for the migraine attack. At a later stage in attacks, aspirin, or the salicylate derived from it, may inhibit prostaglandin synthesis, and thus help relieve pain. There is some evidence that aspirin intake early in the course of migraine attacks is associated with better pain relief than when aspirin is taken later in attacks.

The above quotation if from an article in *Cephalalgia* (1982:2:71-76) entitled "Aspirin Treatment of Migrain Attacks: Clinical Observations" by Ross-Lee L, Eadie M. J., Tyrer J. H.

There is, therefore, a need to provide a personal ready-to-use package, preferably suitable for carrying in a woman's handbag or a man's pants pocket, by which medicine such as aspirin can be delivered by the patient himself into the nasal cavity. This would enable the user to administer the medicine to himself the moment he detected the need, as for instance, the onset of a migraine attack. Preferably such a package can can take the form of a squeeze bottle similar to the nasal anti-inflamatory products widely on the market.

Nasal squeeze bottles now marketed however and, as noted above, have spray-producing nozzles which would not be optimum for the present purpose. Invariably they lead the liquid up to a mixing chamber in which the liquid is blended with air from the bottle above the liquid level. The air breaks up the liquid into fine particles, some of which are so fine that they are inhaled into the lungs and do not remain in the nasal area. For purposes of a respiratory anti-inflamatory or epinephrine this more general application is appropriate.

However, in the present instance more precise delivery to a local area in the nasal cavity is the objective for at least two reasons. First, the dosage of medicines that are to be absorbed into the bloodstream can best be controlled if it is all delivered to the area, namely the permeable tissues in the roof of the nasal cavity which readily absorb the medicine. There is the related drawback of a mist-type spray that in this use delivery of the proper dosage to the desired local area would require many times the necessary number of squeezes, with the majority being diffused over an area in which it would not be effective at all (windpipe, lungs, etc). This would be needlessly burdensome and time-consuming to the user.

Second, some medicines, for instance aspirin, have acid or a basic character which would needlessly irritate the respiratory tissues.

There is need, therefore, to provide in such a medicine dispensing package a nozzle which produces a fountain of large droplets which impact on and remain for the most part on the roof tissues of the nasal cavity, but are large enough so that they do not become entrained in the airstream of the inhaling subjects as do the fine mist-type sprays of the prior art.

SUMMARY OF THE INVENTION

The present invention provides a package by which aspirin, for instance, can be administered into the nasal cavity in the form of a fountain of droplets as is desired for the purpose. A particular feature of the invention is the provision of a swirl chamber by which liquid breakup is accomplished in the absence of air. The package comprises a resilient-walled container having at its upper end a rounded discharge head which is adapted to be inserted into a human nostril. The head has a central opening and an annular wall extending downward from the opening. Across the annular wall is a radial support wall, having an upstanding central post. The post and a discharge orifice element are disposed snugly in the annular wall and engage the top of the post. Together they define a swirl chamber. Extending down from the head is a die tube.

When the rounded discharge head is inserted into a nostril and the container is squeezed, a medical preparation in the container is propelled up the dip tube into the swirl chamber in the absence of air to discharge in a fountain of relatively large droplets to impact on the nasal tissue and be rapidly absorbed thereby into the bloodstream. Preferably, the majority of the droplets are at least above 50 microns.

BRIEF DESCRIPTION OF THE DRAWINGS

Further objectives and features of the invention will be clear from a study of the following specification and the drawings all of which disclose non-limiting embodiments of the invention. In the drawings

DESCRIPTION OF THE PREFERRED EMBODIMENT

Figure 1:
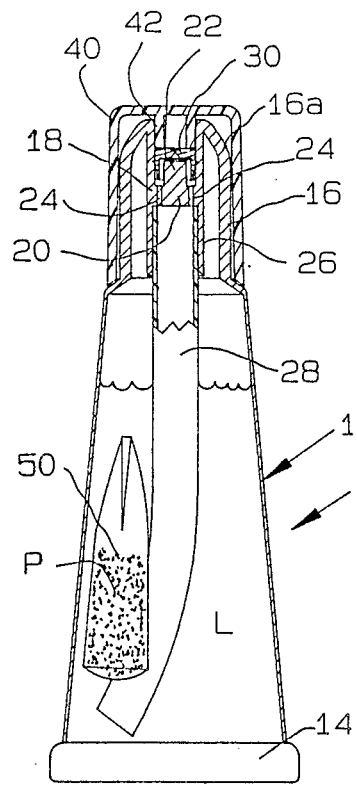
FIG. 1 is a sectional view of a dispensing package embodying the invention as it would appear at time of purchase.
Figure 2:
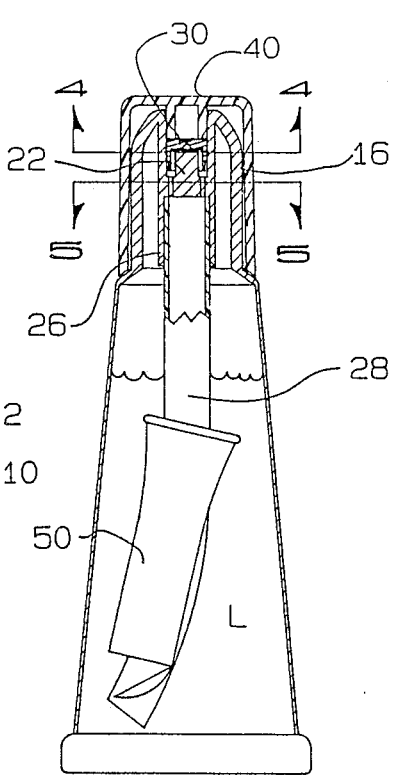
FIG. 2 is similar to FIG. 1 but showing the package ready for use, the inner capsule having been ruptured and its contents mixed in the liquid of the outer container.

A dispensing package embodying the invention is generally designated 10 in FIG. 1. It comprises a tubular resilient wall container 12 sealed flat across the bottom like a toothpaste tube as at 14. The upper end of the container is formed with a discharge head 16 which is rounded as at 16a at its upper end.

The head 16 has a central opening with an annular wall 18 extending downward therefrom. Across the annular wall is a radial support wall 20 which is formed with a central upstanding post 22. A pair of passages 24 are formed through the radial support wall for reasons which will appear. The annular wall 18 is preferably formed with an enlarged opening in its length 26 below the radial support wall.

The structure thus far described may be molded as a single element of plastic, for instance, polyethylene.

A plastic dip tube 28 is sealingly installed into the opening in the length 26 of the annular wall and extends downward into the liquid L which is disposed inside the container 12, its lower end being spaced from the seal 14.

An inverted cup-shaped button 30 is installed in snug fit into the opening in the head 16 preferably the side walls of the button 30 are formed with barbs 32 which dig into the plastic of the annular wall 18 and keep the button in place. The button 30 is a conventional aerosol swirl chamber button found in the dispensing actuator of aerosol valves.

Figure 3:
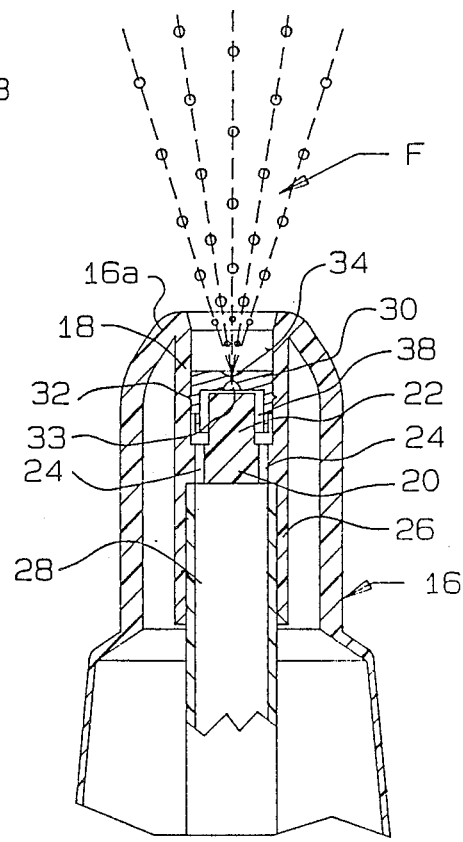
FIG. 3 is an enlarged fragmentary sectional view showing the structure of the dispensing head.
Figure 4:
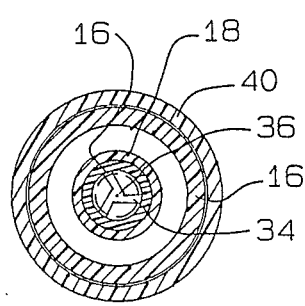
FIG. 4 is a sectional view taken on the line 4—4 of FIG. 2.
Figure 5:
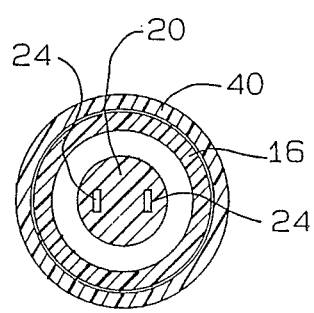
FIG. 5 is a sectional view taken on the line 5—5 of FIG. 2.

The underside of the top wall of the button 30 is formed with channels leading tangentially to the center of the button to form a swirl chamber 33 known in the art. The side walls of the swirl chamber funnel upwardly (FIG. 3) to a discharge orifice 34. The smooth top surface of the post 20 in the embodiment shown forms the bottom wall of the swirl chamber, and channels 38 are formed on the inside of the side wall of the button.

It is an equivalent, foreseeable and reasonable variation that the swirl chamber be formed in the top of the post 22 with the button being in the form of a disc with a central orifice, or a button having a top wall with orifice, the top wall having a flat undersurface.

Completing the assembly is a cap 40 (FIG. 1) which is formed with a center downward plug 42 which fits into the opening at the top of the head 16 in sealing fashion as shown. The lower end of the plug 42 may bottom against the top of the button 30. The side walls of the cup 40 may engage the side wall of the head 16 in frictional engagement to help hold it on.

Inside the container 12, depending on the medicine to be administered, there may be a capsule 50 of powder P. The capsule is rupturable when the dispenser is readied for use, so that the contents of the capsule may, after rupturing, spill into the liquid L permitting the liquid to dissolve the powder, react with it, etc. It should be understood that, depending on the medication, the contents of the capsule 50 may be a liquid, and the outer container 12 may contain a powder. Both can be liquids as well.

The medication may be administered once the preparatory step of rupturing the capsule 50, if present, is taken. In dispensing, the head 16 is inserted in a nostril and the container 12 is then squeezed causing the liquid level to compress air within the container 12 above the liquid level. This air volume serves as a kind of "cushion" and helps deliver the liquid to the discharge head in a more or less predictable rate irrespective of how timidly or vigorously container 12 is squeezed.

The increase of liquid pressure when the container is squeezed drives the liquid up the dip tube 28, through the passages 24, up channels 38 and into the tangential channels 34 to the swirl chamber 33.

In the absence of air the liquid swirls about the swirl chamber and discharges upwardly, its angular velocity increasing as the upper end of the funnel-shaped chamber is approached. The swirl at the orifice is sufficient to break up the emerging liquid and emit in the form of a narrow fountain F of large droplets. Preferably, as stated, the majority of droplets is at least above 50 microns. The squeezing of the container 12 is sufficient to drive the droplets up into the nasal cavity so that they impinge upon the downwardly facing tender tissues in which the blood vessels are virtually at the surface. This impingement effects virtually immediate absorption into the bloodstream.

In actual use, the package may be set up to function as a means to administer aspirin to a nasal cavity. In such a case the capsule 50 is filled with, for instance, 400 mg. of acetylsalicylic acid and the outer container contains a diluent, for instance 4 cc of triethanolamine in an aqueous solution, or a water solution of N-methylglucamine. When the capsule is burst, the acetylsalicylic acid powder run into the liquid and is promptly dissolved.

Figure 6:
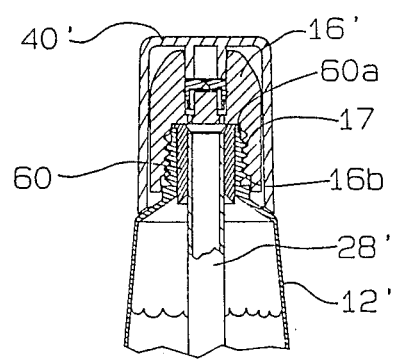
FIG. 6 is a reduced fragmentary sectional view comparable to the upper parts of FIGS. 1 and 2 showing a modified form of the invention.

In FIG. 6 a modified form of the invention is adapted for use as a refillable dispenser. The head 16' is a solid element which is screw-threaded as at 17 to the neck 16b of the container 12'. The dip tube 28' is sealed into a sleeve 60 having a flange 60a which is clamped between the head 16' and the top of the neck 16a of the container 12'. This embodiment may be refilled by unscrewing the head 16', raising the sleeve and dip tube 28' and filling through the neck 17. Thereafter the head 16' may be reinstalled on the neck, and the cap 40' restored to place.

It will be clear that variations from the embodiments described are possible. The invention therefore may be thought of in terms of the scope of the following claim language or equivalents thereof.

What is claimed is:

1. A dispensing package for administering a medical preparation to a human nasal cavity comprising a resilient-walled container having at its upper end a rounded discharge head which is adapted to be inserted into a human nostril, the head having a central opening and an annular wall extending downward from the opening, the annular wall being formed intermediate its ends with a radial support wall, the support wall having an upstanding central post, an inverted cup-shaped button disposed snugly in the annular wall and engaging the top of the post, the button and the top surface of the post between them defining a swirl chamber, the button having a central discharge orifice, central of the chamber and directed upward, a dip tube sealingly disposed in the lower end of the annular wall and extending down into the container, and passage means from the top of the dip tube through the support wall up into the swirl chamber, and a closure adapted to be removably disposed in the central opening in the discharge head, the container enclosing a rupturable capsule containing one composition and the container containing a second composition whereby the container with the closure on can be forcefully squeezed to rupture the capsule and allow its contents to contact the second composition and by inserting the rounded discharge head into a nostril and squeezing the container, a medical preparation in the container can be propelled up the dip tube into the swirl chamber in the absence of air to discharge in a narrow cone of relatively large droplets to land on the nasal tissue and be rapidly absorbed thereby into the blood-stream.

2. A dispensing package as claimed in claim 1 wherein the majority of the droplets are at least above 50 microns in size.

3. A dispensing package as claimed in claim 1 wherein the closure is a plug adapted to fit snugly into the central opening in the discharge head.

4. A dispensing package as claimed in claim 3 wherein the plug is on the top wall of a cap adapted to fit over the sides of the discharge head.

5. A dispensing package as claimed in claim 1 wherein one of the compositions is acetylsalicylic acid and the other is a solution of triethanolamine.

6. A dispensing package as claimed in claim 1 wherein one of the compositions is acetylsalicylic acid and the other is a solution of N-methylglucamine.

7. A dispensing package as claimed in claim 1 wherein the head, the annular wall and the resilient-walled container are all unitary.

8. A dispensing package for administering a medical preparation to a human nasal cavity comprising a resilient-walled container at its upper end a rounded discharge head means which is adapted to be inserted into a human nostril, the head means having a central opening and an annular wall means extending downward from the opening, the annular wall means being formed intermediate its ends with a transverse support wall, the support wall having an upstanding central post, an inverted cup-shaped button disposed snugly in the annular wall and engaging the top of the post, the button and the top surface of the post between them defining a swirl chamber, the button having a central discharge orifice, central of the chamber and directed upward, the wall means including a dip tube extending down into the container, and passage means from the top of the dip tube through the support wall and between the post and button to introduce liquid tangentially into the swirl chamber, and a closure adapted to be removably disposed in the central opening in the discharge head, the container enclosing a rupturable capsule containing one composition and the container containing a second composition whereby the container, with the closure on, can be forcefully squeezed to rupture the capsule and allow its contents to contact the second composition and by inserting the rounded discharge head into a nostril and squeezing the container, a medical preparation in the container can be propelled up the dip tube into the swirl chamber in the absence of air to discharge in a narrow cone of relatively large droplets to land on the nasal tissue and be rapidly absorbed thereby into the blood-stream.

9. A dispensing package for liquids to deliver a product in droplet form, comprising a resilient-walled container, a discharge head on the container, the head including an annular outwardly facing recess defining a central post, a button having a circular wall with a central discharge orifice therethrough and being disposed against the top of the post and sealing the recess, the post and circular wall defining between them a swirl chamber having at least one tangential channel leading to the side of a central circular chamber having its axis in line with the orifice, and a dip tube extending down into the container and having its upper end communicating with the channel as the only passage from the container into the head, whereby when the container is squeezed, liquid in the container is driven up the dip tube into the channel to swirl in the swirl chamber in the absence of air and emerge from the orifice in droplet form.

* * * * *